(12) United States Patent
Park et al.

(10) Patent No.: US 8,399,883 B2
(45) Date of Patent: Mar. 19, 2013

(54) NITROGEN-OXIDE GAS SENSOR WITH LONG SIGNAL STABILITY

(75) Inventors: Jin Su Park, Daejeon (KR); Byung Young Yoon, Chungcheongnam-Do (KR); Jung Won Park, Daejeon (KR); Jung Hwan Cho, Chungcheongnam-Do (KR); Sang Beom Kim, Chungcheongnam-Do (KR)

(73) Assignees: Iljin Copper Foil Co., Ltd., Iksan, Jeollabuk-do (KR); Cios Inc., Daejeon (KR)

( * ) Notice: Subject to any disclaimer, the term of this patent is extended or adjusted under 35 U.S.C. 154(b) by 0 days.

(21) Appl. No.: 13/119,584

(22) PCT Filed: Sep. 30, 2009

(86) PCT No.: PCT/KR2009/005613
§ 371 (c)(1),
(2), (4) Date: Mar. 17, 2011

(87) PCT Pub. No.: WO2010/038987
PCT Pub. Date: Apr. 8, 2010

(65) Prior Publication Data
US 2011/0163314 A1 Jul. 7, 2011

(30) Foreign Application Priority Data

Sep. 30, 2008 (KR) .......... 10-2008-0096088
Sep. 30, 2009 (KR) .......... 10-2009-0093054

(51) Int. Cl.
*G01N 27/406* (2006.01)
(52) U.S. Cl. ..... 257/43; 257/48; 257/414; 257/E29.139; 204/424

(58) Field of Classification Search ................ 204/424; 257/43, 48, 414, E29.139
See application file for complete search history.

(56) References Cited

U.S. PATENT DOCUMENTS
(Continued)

FOREIGN PATENT DOCUMENTS
JP 7-198671 A 8/1995
JP 7-225214 A 8/1995
(Continued)

OTHER PUBLICATIONS
International Search Report: mailed May 7, 2010; PCT/KR2009/005613.
(Continued)

*Primary Examiner* — George Fourson, III
(74) *Attorney, Agent, or Firm* — Ladas & Parry LLP

(57) ABSTRACT

The present invention provides a nitrogen-oxide gas sensor that is able to measure nitric oxide and nitrogen dioxide at the same time and ensure measurement accuracy and long stability. For these purposes, the nitrogen-oxide gas sensor includes: an oxide ion conductive solid electrolyte; a primary film that contacts the solid electrolyte and is made of a p-type semi-conductor metal oxide; a secondary film that contacts the solid electrolyte and is made of a p-type semiconductor metal oxide; an n-type semiconductor metal oxide that is included in at least one of the primary and secondary films; a power source that applies electric power to the primary and secondary films by electrically connecting a primary node to the primary film and a secondary node to the secondary film; and a measurement unit that measures the electric potential difference between the primary and secondary nodes.

14 Claims, 4 Drawing Sheets

U.S. PATENT DOCUMENTS

| | | | |
|---|---|---|---|
| 6,598,596 | B2 | 7/2003 | Wachsman et al. |
| 6,787,014 | B2 | 9/2004 | Hasei et al. |
| 7,537,678 | B2* | 5/2009 | Imanaka ........................ 204/431 |
| 7,678,329 | B2* | 3/2010 | Montgomery et al. .......... 422/52 |
| 7,828,956 | B2* | 11/2010 | Ding et al. ..................... 205/781 |
| 2008/0034842 | A1* | 2/2008 | Lee et al. ...................... 73/31.05 |
| 2008/0053827 | A1* | 3/2008 | Ota ................................ 204/424 |
| 2008/0149499 | A1* | 6/2008 | Ding et al. .................. 205/783.5 |
| 2011/0168557 | A1* | 7/2011 | Park et al. ..................... 204/424 |
| 2011/0210013 | A1* | 9/2011 | Ramaswamy et al. ........ 205/775 |
| 2012/0094030 | A1* | 4/2012 | Maedler et al. ............... 427/448 |

FOREIGN PATENT DOCUMENTS

| | | |
|---|---|---|
| JP | 08-247992 A | 9/1996 |
| JP | 97-47963 A | 12/1997 |
| JP | 11-242014 A | 9/1999 |
| JP | 11-510908 A | 9/1999 |
| JP | 2000-002686 A | 1/2000 |
| JP | 2000-321238 A | 11/2000 |
| JP | 2001-194337 A | 7/2001 |
| JP | 2003-042999 A | 2/2003 |
| JP | 2007-017317 A | 1/2007 |
| KR | 1020000016502 A | 3/2000 |
| WO | 97/42495 A1 | 11/1997 |

OTHER PUBLICATIONS

English translation Japanese Office Action, dated Aug. 3, 2012, Patent Appln. No. 2011-528592.
European Search Report; dated Dec. 12, 2013 Appln. No. 09817997-1-2204/2330412; PCT/KR2009005613.

* cited by examiner

NITROGEN-OXIDE GAS SENSOR WITH LONG SIGNAL STABILITY

TECHNICAL FIELD

The present invention relates to a nitrogen-oxide gas sensor, and more particularly, to a nitrogen-oxide gas sensor which may secure long stability.

BACKGROUND ART

A nitrogen-oxide gas includes nitric oxide (NO), nitrogen dioxide ($NO_2$), and nitrous oxide ($N_2O$) and is represented by NOx. Nitric oxide (NO) and nitrogen dioxide ($NO_2$) are mainly included in the nitrogen-oxide gas and act as atmospheric pollution sources so that a discharge amount thereof may need to be appropriately controlled by measuring the concentration.

A general method of measuring concentration of nitrogen-oxide includes use of equilibrium potential. In the use of the equilibrium potential, solid-state nitrate is formed as a sensing electrode in a solid electrolyte and a noble metal electrode is formed to make ion activity uniform in the solid electrolyte so as to form an electrochemical cell. Thus, an electromotive force generated from the cell is used to measure concentration of nitrogen-oxide. However, such a method is hardly applied to a gas in high-temperature due to low melting point of a sensing electrode.

Another method of measuring concentration of nitrogen-oxide includes use of a current type sensor. In the use of the current type sensor, an oxygen pumping cell is used to convert nitrogen dioxide into nitric oxide, and a current by oxygen ion obtained by decomposing nitric oxide is measured, thereby measuring concentration of nitrogen-oxide. However, in this method, there is structural limitation such as use of an oxygen pumping cell, current measurement by oxygen ion is considerably changed according to temperature, and a measured current is significantly decreased under few hundreds ppm or below so that a total amount of nitrogen-oxide is hardly measured.

Another method of measuring concentration of nitrogen-oxide includes mixed dislocation. In the mixed dislocation, a sensing electrode is formed at one side of an oxygen ion conductive solid electrolyte by using metal oxide, and a reference electrode is formed at the other side of the solid electrolyte by using a noble metal so that a potential difference between the sensing electrode and the reference electrode is measured. That is, the sensing electrode has reactivity against nitrogen-oxide and oxide, whereas the reference electrode only has reactivity against oxygen so that a potential difference between the sensing electrode and the reference electrode is generated according to concentration of nitrogen-oxide included in a gas and thus the potential difference is measured so as to measure concentration of nitrogen-oxide. However, in this method, due to a difference of an electromotive force generated according to decomposition of nitrogen dioxide and nitric oxide, measurement accuracy of a nitrogen-oxide gas including both nitrogen dioxide and nitric oxide is decreased.

In this regard, a method of using a conversion cell that convert nitrogen-oxide into one gas type has been suggested. However, there is a limit to covert entire nitrogen-oxide into nitric oxide or nitrogen dioxide and thus it is hard to measure concentration of nitrogen-oxide.

DETAILED DESCRIPTION OF THE INVENTION

Technical Problem

Figure 1:
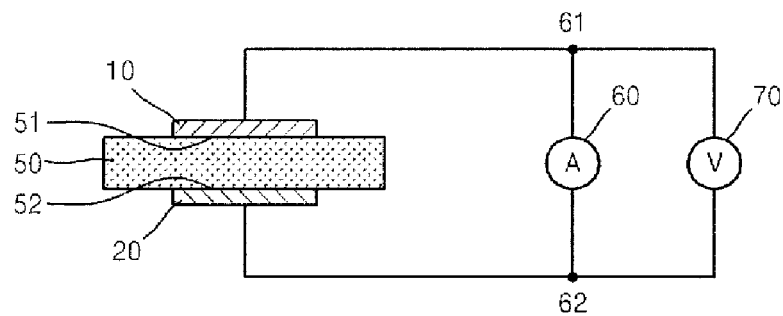
FIG. 1 schematically illustrates a nitrogen-oxide gas sensor, according to an embodiment of the present invention.

The present invention provides a nitrogen-oxide gas sensor that is able to measure nitric oxide and nitrogen dioxide at the same time and ensures measurement accuracy and long stability.

Technical Solution

According to an aspect of the present invention, there is provided a nitrogen-oxide gas sensor including: an oxide ion conductive solid electrolyte; a first film that contacts the solid electrolyte and is made of a p-type semiconductor metal oxide; a second film that contacts the solid electrolyte and is made of a p-type semiconductor metal oxide; an n-type semiconductor metal oxide that is included in at least one of the first and second films; a power source that applies electric power to the first and second films by electrically connecting a first node to the first film and a second node to the second film; and a measurement unit that measures the electric potential difference between the first and second nodes.

The n-type semiconductor metal oxide may be formed by mixing the p-type semiconductor metal oxide of at least one of the first and second films.

The n-type semiconductor metal oxide may be formed by solid solution treating the p-type semiconductor metal oxide of at least one of the first and second films.

One of the first and second films that includes the n-type semiconductor metal oxide may be formed as a stack body of a film comprising the p-type semiconductor metal oxide and a buffer film comprising the n-type semiconductor metal oxide.

The buffer film may be formed as a solid solution of the n-type semiconductor metal oxide and the p-type semiconductor metal oxide.

The buffer film may be formed as a mixture of the n-type semiconductor metal oxide and the p-type semiconductor metal oxide.

The nitrogen-oxide gas sensor may further include a first electrode that is formed on a surface of the first film facing the solid electrolyte and is formed of a conductive metal.

The nitrogen-oxide gas sensor may further include a third film that contacts the solid electrolyte, is formed of a conductive metal, and is connected to the first film in parallel with respect to the power source.

The first electrode and the third film may be integrally formed with each other as a single body.

The first electrode and the third film may each be formed of a noble metal.

The nitrogen-oxide gas sensor may further include a second electrode that is formed on a surface of the second film facing the solid electrolyte and is formed of a conductive metal.

The nitrogen-oxide gas sensor may further include a fourth film that contacts the solid electrolyte, is formed of a conductive metal, and is connected to the second film in parallel with respect to the power source.

The second electrode and the fourth film may be integrally formed with each other as a single body.

The second electrode and the fourth film may each be formed of a noble metal.

Advantageous Effects

According to the present invention, nitric oxide and nitrogen dioxide may be measured at the same time by first and second films.

Also, measurement accuracy may be increased by a third film connected in parallel to a first film and a fourth film connected in parallel to a second film.

In addition, a p-type semiconductor metal oxide is used as the first film, another p-type semiconductor metal oxide is used as a second film, and an n-type semiconductor metal oxide is included in at least one of the first and second films, thereby ensuring long stability.

BEST MODE

Hereinafter, the exemplary embodiments of the present invention will b described in detail.

The present invention may, however, be embodied in many different forms and should not be construed as being limited to the embodiments set forth herein; rather, these embodiments are provided so that this disclosure will be thorough and complete, and will fully convey the concept of the invention to those skilled in the art.

FIG. 1 schematically illustrates a nitrogen-oxide gas sensor, according to an embodiment of the present invention.

Referring to FIG. 1, the nitrogen-oxide gas sensor according to the current embodiment of the present invention includes an oxygen ion conductive solid electrolyte 50, a first film 10 and a second film 20 each contacting the oxygen ion conductive solid electrolyte 50, a power source 60, and a measurement unit 70.

The oxygen ion conductive solid electrolyte 50 allows conduction of oxygen ion at high temperature and may include stabilized zirconia, CeO2, or ThO2. The stabilized zirconia may be, for example, Yttria-stabilized Zirconia (YSZ).

The first film 10 contacts a first region 51 of the oxygen ion conductive solid electrolyte 50 and the second film 20 contacts a second region 52 of the oxygen ion conductive solid electrolyte 50.

The first film 10 and the second film 20 are each formed of a material having reactivity with respect to nitrogen-oxide and oxygen when a power source is applied thereto. The first film 10 and the second film 20 each include a p-type semiconductor metal oxide. Here, the second film 20 includes another p-type semiconductor metal oxide that is different from the first film 10; however, the present invention is not limited thereto.

The first film 10 may include a p-type semiconductor metal oxide and may include, for example, at least one material selected from the group, mixtures obtained by mixing at least two materials selected from the group, or a mixtures obtained by mixing the oxygen ion conductive solid electrolyte material and at least one material selected from the group, the group consisting of $CuO$, $NiO$, $CoO$, $Cr_2O_3$, $Cu_2O$, $MoO_2$, $Ag_2O$, $Bi_2O_3$, $Pr_2O_3$, $MnO$, and $LaCoO_3$. In the exemplary embodiment of the present invention, the first film 10 may include NiO from among the p-type semiconductor metal oxides.

The second film 20 contacts the second region 52 of the oxygen ion conductive solid electrolyte 50. The second film 20 may also include a p-type semiconductor metal oxide and may include, for example, at least one material selected from the group, mixtures obtained by mixing at least two materials selected from the group, or a mixtures obtained by mixing the oxygen ion conductive solid electrolyte material and at least one material selected from the group, the group consisting of $CuO$, $NiO$, $CoO$, $Cr_2O_3$, $Cu_2O$, $MoO_2$, $Ag_2O$, $Bi_2O_3$, $Pr_2O_3$, $MnO$, and $LaCoO_3$. In the exemplary embodiment of the present invention, the second film 20 may include another p-type semiconductor metal oxide that is different from the first film 10, for example, $CuO$ or $LaCoO_3$.

In FIG. 1, the first region 51 and the second region 52 face each other based on the oxygen ion conductive solid electrolyte 50; however, the present invention is not limited thereto. The first region 51 and the second region 52 may be disposed in each different region on the same plane of the oxygen ion conductive solid electrolyte 50. In this regard, the first region 51 and the second region 52 may not be overlapped with each other, as will be described in detail later.

The first film 10 and the second film 20 may be electrically connected to a first node 61 and a second node 62, respectively, so that a uniform current may be applied thereto.

In the present invention, the first film 10 may be used as a positive electrode and the second film 20 may be used as a negative electrode.

Anodic reaction, in which oxygen ion is converted into an oxygen gas, occurs in the interface between the first film 10 as a positive electrode and the oxygen ion conductive solid electrolyte 50, and when a NO gas exists at the same time, anodic reaction occurs by NO as represented in Reaction Formula 1 and intensity of voltage for flowing an uniform current decreases Here, anodic polarization is applied to the first film 10 so that reaction to NO increases and reaction to $NO_2$ decreases.

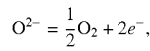
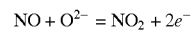

[Reaction Formula 1]

$$O^{2-} = \frac{1}{2}O_2 + 2e^-,$$
$$NO + O^{2-} = NO_2 + 2e^-$$

Cathodic reaction, in which an oxygen gas is converted into oxygen ion, occurs in the interface between the second film 20 as a negative electrode and the oxygen ion conductive solid electrolyte 50, and when a $NO_2$ gas exists at the same time, cathodic reaction occurs by $NO_2$ as represented in Reaction Formula 2 and intensity of voltage for flowing an uniform current decreases. Here, cathodic polarization is applied to the second film 20 so that reaction to $NO_2$ increases and reaction to NO decreases.

[Reaction Formula 2]

$$\frac{1}{2}O_2 + 2e^- = O^{2-},$$

$$NO_2 + 2e^- \Rightarrow NO + O^{2-}$$

According to the present invention, when a mixture gas of NO and $NO_2$ exists, measurement accuracy for both gases may increase.

Also, the measurement unit 70 is connected to the first node 61 and the second node 62 and thus measures a potential difference between the first node 61 and the second node 62.

In such a structure, when the first film 10 and the second film 20 are exposed to a nitrogen-oxide mixture gas at high temperature, a potential difference changes according to concentrations of nitrogen dioxide and nitric oxide in the nitrogen-oxide gas and the total concentration of nitrogen dioxide and nitric oxide may be measured.

As described above, when the first film 10 and the second film 20 are formed of a p-type semiconductor metal oxide, measurement unstability of a sensor may occur. Since both the first film 10 and the second film 20 use a p-type semiconductor metal oxide, concentration of holes is higher than concentration of electrons and thereby, gas reaction speed is gradually decreased due to lack of electrons. Thus, voltage for a uniform current increases according to time. In this regard, electron concentration of a p-type semiconductor metal oxide, which is a sensing material, needs to be increased. In the present invention, at least one of the first film 10 and the second film 20 is formed of a solid solution of a p-type semiconductor metal oxide and an n-type semiconductor metal oxide or a mixture of a p-type semiconductor metal oxide and an n-type semiconductor metal oxide, or a buffer layer 11 including an n-type semiconductor metal oxide is interposed between the at least one of the first film 10 and the second film 20 and the oxygen ion conductive solid electrolyte 50. Here, the n-type semiconductor metal oxide may include at least one metal oxide selected from the group consisting of ZnO, MgO, $Al_2O_3$, $SiO_2$, $V_2O_5$, $Fe_2O_3$, SrO, BaO, $TiO_2$, $BaTiO_3$, $CeO_2$, $Nb_2O_5$, $Ta_2O_5$, $Ga_2O_3$, and $WO_3$ or mixtures thereof. According to an embodiment of the present invention, the n-type semiconductor metal oxide may be ZnO.

Accordingly, in FIG. 1, the first film 10 is manufactured by mixing the p-type semiconductor metal oxide and the n-type semiconductor metal oxide or by solid solution treating the p-type semiconductor metal oxide and the n-type semiconductor metal oxide. Then, long stability of the first film 10 may be secured. The second film 20 is similar to the first film 10. An n-type semiconductor metal oxide may be only mixed or solid solution treated in the second film 20 or an n-type semiconductor metal oxide may be mixed or solid solution treated in both the first film 10 and the second film 20. Here, the p-type semiconductor metal oxide is mainly mixed or solid solution treated or the n-type semiconductor metal oxide is mainly mixed or solid solution treated.

Figure 2:
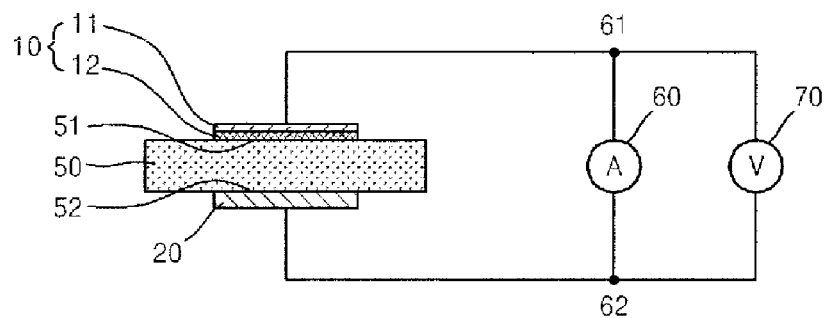
FIG. 2 schematically illustrates a nitrogen-oxide gas sensor, according to another embodiment of the present invention.

As illustrated in FIG. 2, the n-type semiconductor metal oxide may be a buffer film 12 interposed between a film 11 including the p-type semiconductor metal oxide and the oxygen ion conductive solid electrolyte 50, and the first film 10 may be formed as a stack body of the film 11 and the buffer film 12. Here, the film 11 including the p-type semiconductor metal oxide may include at least one material selected from the group, mixtures obtained by mixing at least two materials selected from the group, or a mixtures obtained by mixing the oxygen ion conductive solid electrolyte material and at least one material selected from the group, the group consisting of CuO, NiO, CoO, $Cr_2O_3$, $Cu_2O$, $MoO_2$, $Ag_2O$, $Bi_2O_3$, $Pr_2O_3$, MnO, and $LaCoO_3$.

Also, the n-type semiconductor metal oxide used in the buffer film 12 may include at least one metal oxide selected from the group consisting of ZnO, MgO, $Al_2O_3$, $SiO_2$, $V_2O_5$, $Fe_2O_3$, SrO, BaO, $TiO_2$, $BaTiO_3$, $CeO_2$, $Nb_2O_5$, $Ta_2O_5$, $Ga_2O_3$, and $WO_3$ or mixtures thereof. According to an embodiment of the present invention, the n-type semiconductor metal oxide may be ZnO.

The buffer film 12 may be a solid solution of the p-type semiconductor metal oxide and the n-type semiconductor metal oxide or a mixture of the p-type semiconductor metal oxide and the n-type semiconductor metal oxide. For example, the film 11 formed of the p-type semiconductor metal oxide may include NiO, and a NiO-ZnO solid solution is used as the buffer film 12, thereby forming the first film 10. In this case, the buffer film 12 may increase mechanical connection of the first film 10 with the oxygen ion conductive solid electrolyte 50.

As described above, since the buffer film 12 is interposed between the film 11 formed of the p-type semiconductor metal oxide and the oxygen ion conductive solid electrolyte 50, measurement unstability of a sensor may be prevented, deterioration of the first film 10 may slow down, and thereby long stability may be ensured.

In FIG. 2, the first film 10 is illustrated as a stack body of the film 11 including the p-type semiconductor metal oxide and the buffer film 12; however, the present invention is not limited thereto. Although not illustrated, the second film 20 may also be disposed as a stack body.

In FIGS. 1 and 2, the first film 10 and the second film 20 are wire bonded to the first node 61 and the second node 62, respectively. That is, a bonding pad is each formed on the first film 10 and the second film 20 by using conductive polymer or other conductive member and a wire power line is connected to the bonding pad.

Figure 3:
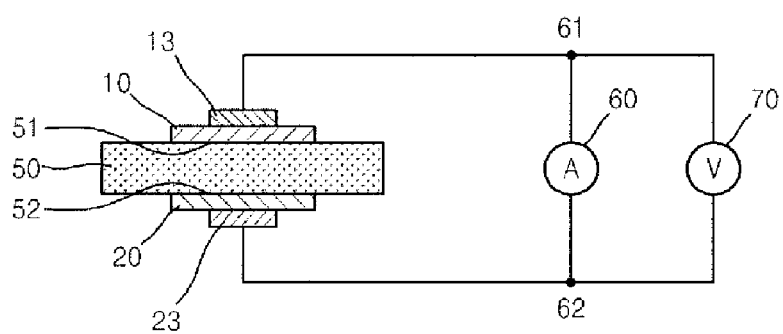
FIG. 3 schematically illustrates a nitrogen-oxide gas sensor, according to another embodiment of the present invention.
Figure 4:
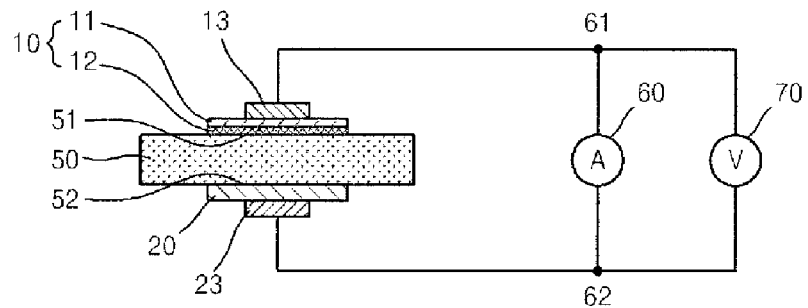
FIG. 4 schematically illustrates a nitrogen-oxide gas sensor, according to another embodiment of the present invention.

FIGS. 3 and 4 schematically illustrate a nitrogen-oxide gas sensor, according to other embodiments of the present invention. In FIGS. 3 and 4, a first electrode 13 is formed on the first film 10 so as to electrically connect the first electrode 13 to the first node 61. Also, a second electrode 23 is formed on the second film 20 so as to electrically connect the second electrode 23 to the second node 62. The first electrode 13 and the second electrode 23 may be formed of an electrically conductive metal, for example, a noble metal for enduring corrosion environment. Examples of the noble metal may include at least one selected from the group consisting of gold (Au), silver (Ag), platinum (Pt), iridium (Ir), palladium (Pd), and alloys thereof, and may be gold (Au) or platinum (Pt).

Figure 5:
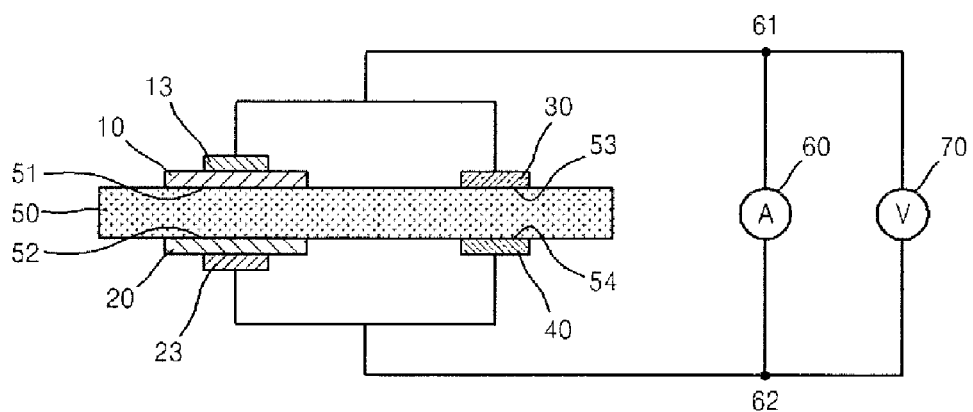
FIG. 5 schematically illustrates a nitrogen-oxide gas sensor, according to another embodiment of the present invention.
Figure 6:
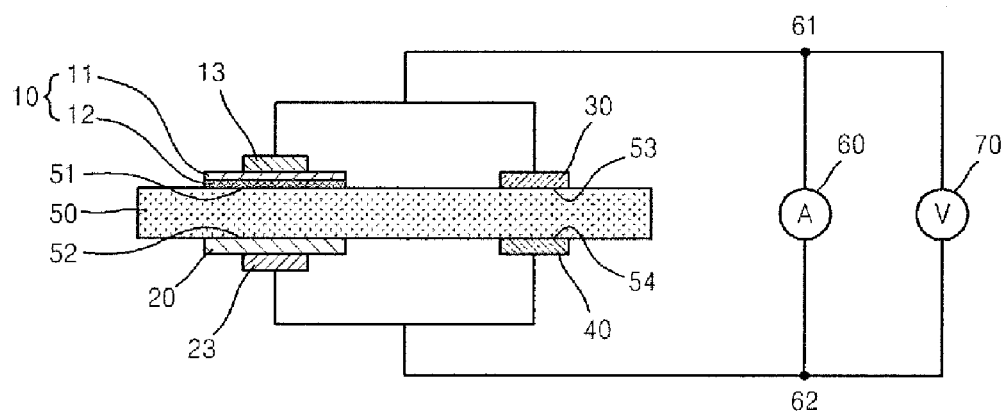
FIG. 6 schematically illustrates a nitrogen-oxide gas sensor, according to another embodiment of the present invention.

FIGS. 5 and 6 schematically illustrate a nitrogen-oxide gas sensor, according to other embodiments of the present invention. In FIGS. 5 and 6, a third film 30 and a fourth film 40 are installed to contact a third region 53 and a fourth region 54 of the oxygen ion conductive solid electrolyte 50, respectively. The first film 10 and the second film 20 in FIGS. 5 and 6 are the same as those of previous embodiments and thus, hereinafter, the third region 53 and the fourth region 54 will be mainly described.

As illustrated in FIGS. 5 and 6, the third region 53 and the fourth region 54 may face each other; however, the present invention is not limited thereto. The third region 53 and the fourth region 54 may be formed on the same plane or each different plane as long as the third region 53 and the fourth region 54 are not overlapped with each other.

The third film 30 and the fourth film 40 may be each formed of an electrically conductive metal, for example, a noble metal for enduring corrosion environment. Examples of the noble metal may include at least one selected from the group consisting of gold (Au), silver (Ag), platinum (Pt), iridium (Ir), palladium (Pd), and alloys thereof, and may be gold (Au) or platinum (Pt). The third film 30 and the fourth film 40 pass excessive electric charge generated in the electrodes due to appliance of a forced current being generated from the first film 10 and the interface between the second film 20 and the oxygen ion conductive solid electrolyte 50 using oxygen substitution reaction in the noble metal and thus ensure stability of a sensor signal.

Here, the third film 30 is electrically connected to the first node 61 so that the power source 60 is connected to the first film 10 in parallel. Also, the fourth film 40 is electrically connected to the second node 62 so that the power source 60 is connected to the second film 20 in parallel. Also, the measurement unit 70 is connected to the first node 61 and the second node 62 and thus measures a potential difference between the first node 61 and the second node 62.

As described above, the first film 10 and the third film 30, and the second film 20 and the fourth film 40 are each connected to each other in parallel so that a measurement error may be reduced and long stability may be increased. This is because since the first film 10 and the third film 30, and the second film 20 and the fourth film 40 are each connected to each other in parallel, the first film 10 and the second film 20 may disperse excessive electric charge accumulated in the oxygen ion conductive solid electrolyte 50 to the third film 30 and the fourth film 40, respectively. However, the present invention is not limited thereto and there may be other complex or unknown reasons.

As illustrated in FIGS. 5 and 6, the third film 30 and the fourth film 40 may not exists as a single film and may each be formed of a plurality of films. Here, a plurality of third films 30 may be connected to each other in parallel and a plurality of fourth films 40 may be also connected to each other in parallel.

Figure 7:
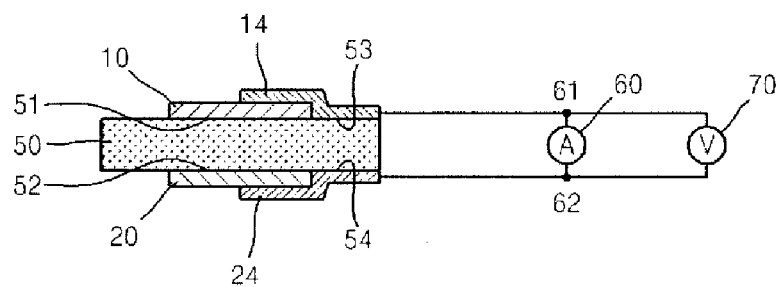
FIG. 7 schematically illustrates a nitrogen-oxide gas sensor, according to another embodiment of the present invention.

FIG. 7 schematically illustrates a nitrogen-oxide gas sensor, according to another embodiment of the present invention. In the nitrogen-oxide gas sensor of FIG. 7, the first film 10 and the second film 20 are formed on the oxygen ion conductive solid electrolyte 50, as illustrated in FIG. 1, and then, a first conductive film 14 and a second conductive film 24 are formed to partially cover the first film 10 and the second film 20 as a thin film, respectively. The first conductive film 14 and the second conductive film 24 may be patterned to be thin films using a conductive material and may function as wirings of the first film 10 and the second film 20, respectively. Accordingly, the first conductive film 14 and the second conductive film 24 may be formed of a noble metal for enduring corrosion environment. Examples of the noble metal may include at least one selected from the group consisting of gold (Au), silver (Ag), platinum (Pt), iridium (Ir), palladium (Pd), and alloys thereof. For example, the first conductive film 14 and the second conductive film 24 may be patterned by coating platinum (Pt) paste.

In this case, a part of the first conductive film 14 that covers the first film 10 may function as a first electrode of the first film 10, as illustrated in FIG. 3, and a part of the first conductive film 14 that contacts the third region 53 of the oxygen ion conductive solid electrolyte 50 may function as a third electrode, as illustrated in FIG. 5. Similarly, a part of the second conductive film 24 that covers the second film 20 may function as a second electrode of the second film 20, as illustrated in FIG. 3, and a part of the second conductive film 24 that contacts the fourth region 54 of the oxygen ion conductive solid electrolyte 50 may function as a fourth electrode, as illustrated in FIG. 5.

Figure 8:
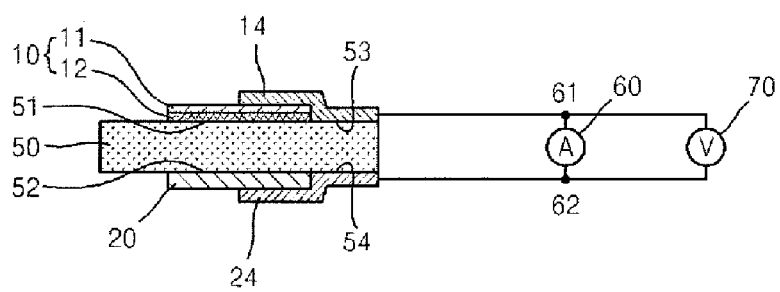
FIG. 8 schematically illustrates a nitrogen-oxide gas sensor, according to another embodiment of the present invention.

The first film 10 and/or the second film 20 illustrated in FIG. 7 may be formed as a stack body of the film 11 including the p-type semiconductor metal oxide and the buffer film 12, as illustrated in FIG. 8. The other elements are the same as those of FIG. 7 and thus detailed description thereof is omitted.

Figure 9:
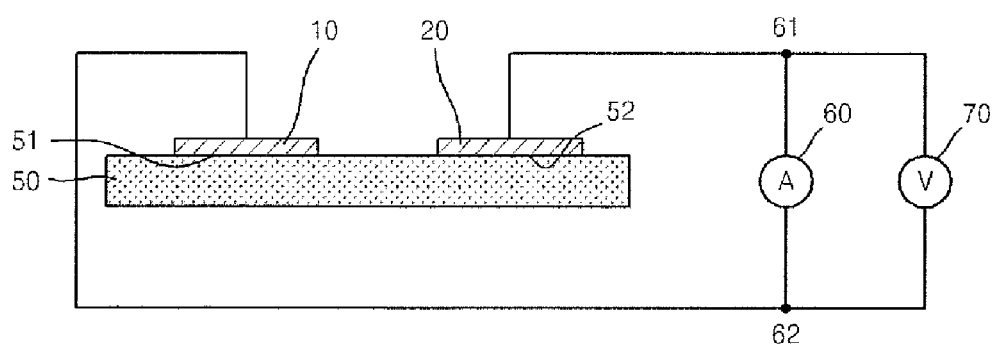
FIG. 9 schematically illustrates a nitrogen-oxide gas sensor, according to another embodiment of the present invention.

As illustrated in FIG. 9, the first film 10 and the second film 20 may be respectively formed to contact the first region 51 and the second region 52 that are disposed on the same plane of the oxygen ion conductive solid electrolyte 50.

The embodiment of FIG. 9 may be applied to the embodiments of FIGS. 2 through 9.

In the embodiments according to FIGS. 1 through 9, the first film 10 and the second film 20 may not exist as a single film and may each be formed of a plurality of films.

Here, a plurality of first films 10 may be connected to each other in parallel and a plurality of second films 20 may be also connected to each other in parallel.

Figure 10:
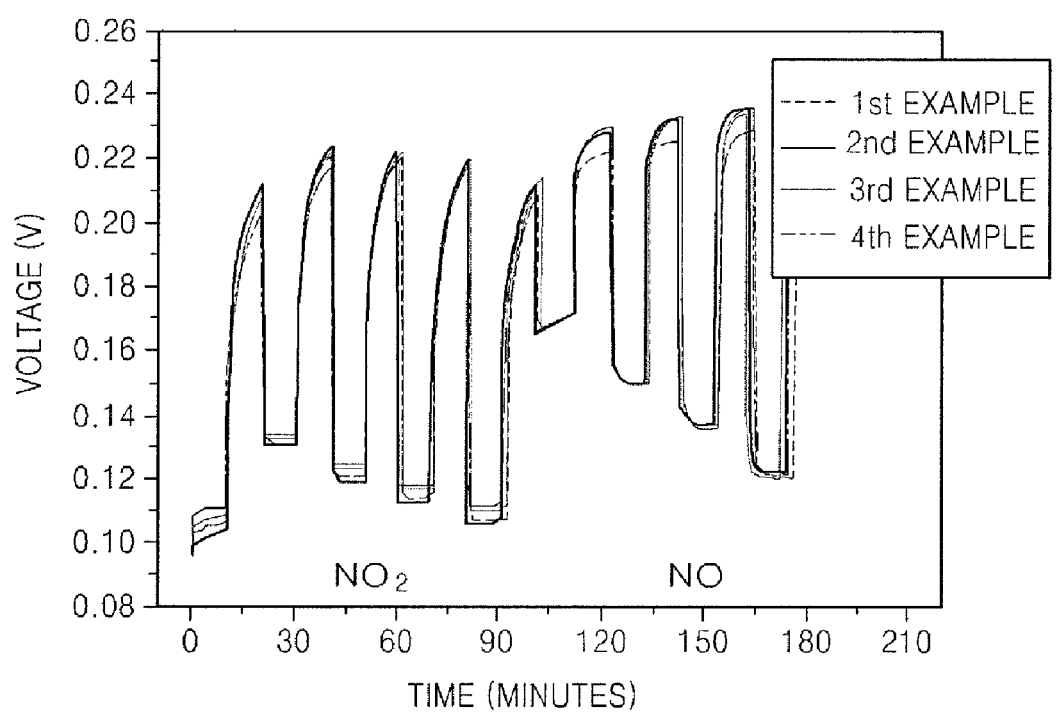
FIG. 10 is a graph illustrating sensing results of a mixture gas of NO and $NO_2$ with respect the nitrogen-oxide gas sensor of FIG. 6.

FIG. 10 is a graph illustrating sensing results of a mixture gas of NO and $NO_2$ with respect the nitrogen-oxide gas sensor of FIG. 6. CuO is used as the second film 20, NiO is used as the film 11 including the p-type semiconductor metal oxide and a NiO—ZnO solid solution is used as the buffer film 12 in the first film 10, platinum (Pt) is used as the first electrode 13, second electrode 23, the third film 30, and the fourth film 40, and YSZ is used as the oxygen ion conductive solid electrolyte 50.

In the sensor having the above structure, voltage is measured while oxygen partial pressure is 20% at temperature of about 700° C. and a constant current of 2.0 µA is applied.

As illustrated in FIG. 10, approximately uniform characteristics may be obtained from four experimental examples and electric potentials are not significantly changed as time passes.

According to the present invention, even if a nitrogen-oxide gas sensor is used for long period of time, accuracy may be maintained.

The invention claimed is:

1. A nitrogen-oxide gas sensor comprising:
an oxide ion conductive solid electrolyte;
a first film that contacts the solid electrolyte and is made of a p-type semiconductor metal oxide;
a second film that contacts the solid electrolyte and is made of a p-type semiconductor metal oxide; an n-type semiconductor metal oxide that is included in at least one of the first and second films; a power source that applies electric power to the first and second films by electrically connecting a first node to the first film and a second node to the second film; and a measurement unit that measures the electric potential difference between the first and second nodes.

2. The nitrogen-oxide gas sensor of claim 1, wherein the n-type semiconductor metal oxide is formed by mixing the p-type semiconductor metal oxide of at least one of the first and second films.

3. The nitrogen-oxide gas sensor of claim 1, wherein the n-type semiconductor metal oxide is formed by solid solution treating the p-type semiconductor metal oxide of at least one of the first and second films.

4. The nitrogen-oxide gas sensor of claim 1, wherein one of the first and second films that comprises the n-type semiconductor metal oxide is formed as a stack body of a film comprising the p-type semiconductor metal oxide and a buffer film comprising the n-type semiconductor metal oxide.

5. The nitrogen-oxide gas sensor of claim 4, wherein the buffer film is formed as a solid solution of the n-type semiconductor metal oxide and the p-type semiconductor metal oxide.

6. The nitrogen-oxide gas sensor of claim 4, wherein the buffer film is formed as a mixture of the n-type semiconductor metal oxide and the p-type semiconductor metal oxide.

7. A nitrogen-oxide gas sensor comprising:
an oxide ion conductive solid electrolyte;
a first film that contacts the solid electrolyte and is made of a p-type semiconductor metal oxide;
a second film that contacts the solid electrolyte and is made of a p-type semiconductor metal oxide;
an n-type semiconductor metal oxide that is included in at least one of the first and second films;
a power source that applies electric power to the first and second films by electrically connecting a first node to the first film and a second node to the second film;
a measurement unit that measures the electric potential difference between the first and second nodes; and
a first electrode that is formed on a surface of the first film facing the solid electrolyte and is formed of a conductive metal.

8. The nitrogen-oxide gas sensor of claim 7, further comprising a third film that contacts the solid electrolyte, is formed of a conductive metal, and is connected to the first film in parallel with respect to the power source.

9. The nitrogen-oxide gas sensor of claim 8, wherein the first electrode and the third film are integrally formed with each other as a single body.

10. The nitrogen-oxide gas sensor of claim 8, wherein the first electrode and the third film are each formed of a noble metal.

11. A nitrogen-oxide gas sensor comprising:
an oxide ion conductive solid electrolyte;
a first film that contacts the solid electrolyte and is made of a p-type semiconductor metal oxide;
a second film that contacts the solid electrolyte and is made of a p-type semiconductor metal oxide;
an n-type semiconductor metal oxide that is included in at least one of the first and second films;
a power source that applies electric power to the first and second films by electrically connecting a first node to the first film and a second node to the second film;
a measurement unit that measures the electric potential difference between the first and second nodes; and
a second electrode that is formed on a surface of the second film facing the solid electrolyte and is formed of a conductive metal.

12. The nitrogen-oxide gas sensor of claim 11, further comprising a fourth film that contacts the solid electrolyte, is formed of a conductive metal, and is connected to the second film in parallel with respect to the power source.

13. The nitrogen-oxide gas sensor of claim 12, wherein the second electrode and the fourth film are integrally formed with each other as a single body.

14. The nitrogen-oxide gas sensor of claim 12, wherein the second electrode and the fourth film are each formed of a noble metal.

* * * * *